US006946644B2

(12) United States Patent
Wood

(10) Patent No.: US 6,946,644 B2
(45) Date of Patent: Sep. 20, 2005

(54) SENSOR FOR MULTI-BAND RADIATION DETECTION WITHIN A FIELD OF VIEW

(75) Inventor: Roland A. Wood, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 286 days.

(21) Appl. No.: 10/324,314

(22) Filed: Dec. 19, 2002

(65) Prior Publication Data

US 2005/0178952 A1 Aug. 18, 2005

(51) Int. Cl.[7] .................................................. G01J 3/50
(52) U.S. Cl. ....................................... 250/226; 250/216
(58) Field of Search ................................ 250/226, 216, 250/239, 214.1, 214 R, 203.4, 221

(56) References Cited

U.S. PATENT DOCUMENTS

| | | | | |
|---|---|---|---|---|
| 4,472,239 A | | 9/1984 | Johnson et al. | |
| 5,220,189 A | | 6/1993 | Higashi et al. | |
| 5,877,500 A | * | 3/1999 | Braig et al. | 250/353 |
| 5,895,233 A | | 4/1999 | Higashi et al. | |
| 6,157,404 A | | 12/2000 | Marshall et al. | |
| 6,277,666 B1 | | 8/2001 | Hays et al. | |
| 6,770,865 B2 | * | 8/2004 | Wootton et al. | 250/226 |
| 2002/0024664 A1 | | 2/2002 | Yokota et al. | |

FOREIGN PATENT DOCUMENTS

| | | |
|---|---|---|
| EP | 0809298 | 11/1997 |
| EP | 0973019 | 1/2000 |
| EP | 1022551 | 7/2000 |

OTHER PUBLICATIONS

Flanigan, Dennis F., "Detection of organic vapors with active and passive sensors: a comparison," Applied Optics, vol. 25 No. 23, pp. 4253-4260, Dec. 1, 1986.

Flanigan, Dennis F., "Prediction of the limits of detection of hazardous vapors by passive infrared with the use of MODTRAN," Applied Optics, vol. 35, No. 30, pp. 6090-6098, Oct. 20, 1996.

Foote, et al., "High performance micromachined thermopile linear arrays," APIE vol. 3379, Part of the SPIE Conference on Infrared Detectors and Focal Plane Arrays V., Orlando, Florida, pp. 192-197, Apr. 1998.

Foote, et al., "Uncooled Thermopile Infrared Detector Linear Arrays with Detectivity Greater than $10^9$ $cmHz^{1/2}$/W," IEEE Transactions on Electron Devices, vol. 45, No. 9, pp. 1896-1902, Sep. 1998.

(Continued)

*Primary Examiner*—Que T. Le
(74) *Attorney, Agent, or Firm*—Kris Fredrick

(57) ABSTRACT

A sensor having a several groups of detectors for gas, agent or interferent detection. The detectors may have various fields of view. The detectors may be placed in particular locations of an array and connected in a certain way as groups such that the resultant groups have essentially the same fields of view. The detectors of a group may be sensitive to the same wavelength of radiation. The array of detectors may be placed in a vacuum sealed package having a substrate and a topcap. The topcap may have bandpass filters on the inside surface over the respective filters for selecting the wavelength of radiation that each detector may detect.

38 Claims, 18 Drawing Sheets

OTHER PUBLICATIONS

Kruse, Application of Uncooled Monolithic Thermoelectric Linear Arrays to Imaging Radiometers, Uncooled Infrared Imaging Arrays and Systems, Semiconductors and Semimetals, vol. 47, Chapter 10, pp. 297-318, Copyright 1997 by Academic Press.

Teranishi, "Thermoelectric Uncooled Infrared Focal Plane Arrays," Uncooled Infrared Imaging Arrays and Systems, Semiconductors and Semimetals, vol. 47, Chapter 6, pp. 203*218, Copyright 1997 by Academic Press.

* cited by examiner

Weight Calculation for single-band Chemical Agent sensor

| | Length (mm) | Width (mm) | Thickness (mm) | Volume (cc) | Density (gm/cc) | Wt (gm) |
|---|---|---|---|---|---|---|
| 30x30 TE mosaic array | 5 | 5 | 0.5 | 0.013 | 2.34 | 0.030 |
| IVP top cap | 4 | 5 | 0.4 | 0.008 | 2.34 | 0.019 |
| Preamps | 5 | 5 | 0.4 | 0.01 | 2.34 | 0.024 |
| Micro Processor | 5 | 10 | 0.4 | 0.02 | 2.34 | 0.048 |
| Misc. chips | 25 | 25 | 0.4 | 0.25 | 2.34 | 0.59 |
| Resistors and capacitors | | | | 0.5 (est.) | 2.5(est.) | 1.25 |
| Gold traces | 25 | 25 | 0.05 | 0.031 | 19.31 | 0.60 |
| Ceramic motherboard | 10 | 10 | 0.5 | 0.05 | 4.0 | 0.20 |
| PbSn solder | 25 | 15 | 0.2 | 0.075 | 11.4 | 0.855 |
| Optical baffles | 20 | 0.1 | 0.1 | 0.0002 | 4.5 | 0.001 |
| Ge window | 10 | 10 | 0.5 | 0.05 | 5.33 | 0.27 |
| Total Weight (gm) | | | | | | 3.89 |

*Fig.13*

SENSOR FOR MULTI-BAND RADIATION DETECTION WITHIN A FIELD OF VIEW

BACKGROUND

The invention pertains to sensors and in particular to sensors for detecting the presence of fluids and other substances. More particularly, the invention pertains to sensors that have detector sensitivities of at least two bandwidths. "Fluid" is a generic term that includes liquids and gases as species. For instance, air, water, oil, gas and agents may be fluids.

The related art might detect at several wavelengths; however, the results of detection may not be sufficiently accurate because of sensor structure or other impediments resulting in different fields of view for detection at different wavelengths.

SUMMARY

The present invention solves the potential field of view problems by utilizing several groups of detectors, wherein the detectors of each group have various a fields of view which may be reflective of their position in an array on a structure. Each group may have an average, resultant or cumulative field of view that is approximately equivalent or the same as a field of view of another group of detectors. Connection and location of the individual detectors on the supporting structure may lead to equivalency or sameness of the fields of views of the numerous groups of detectors.

BRIEF DESCRIPTION OF THE DRAWING

FIG. 13 is a table of dimensions for a sensor.

DESCRIPTION

Figure 1A:
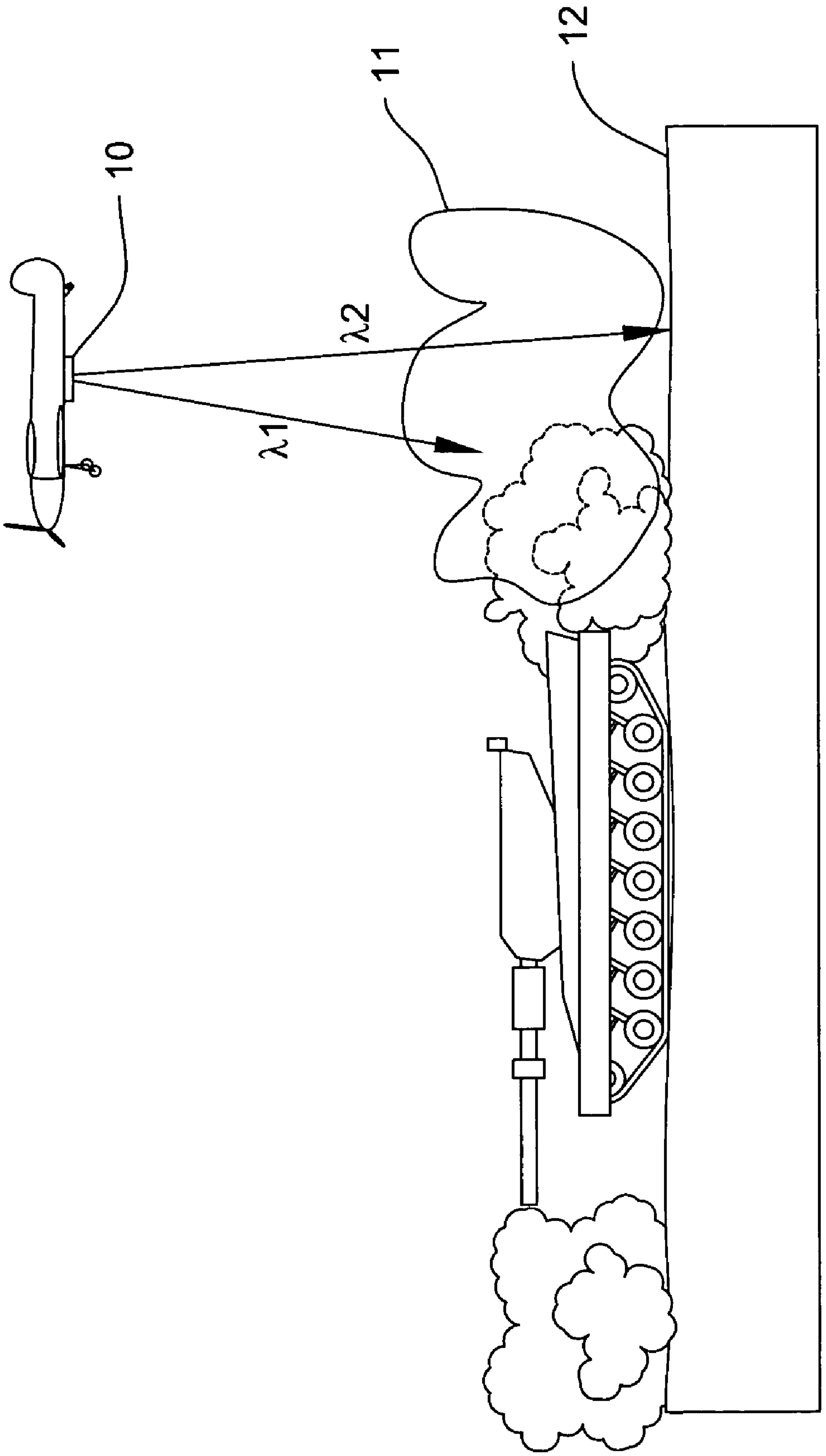
FIGS. 1*a*, 1*b* and 1*c* show upward and downward fields of view for a sensor.

The present invention is a multi-band sensor for chemical agents or other substances in the atmosphere, suitable for flight on micro air vehicles (MAVs), dispersal from aircraft, or other low-cost light-weight applications. The sensor may sense the infrared (IR) emission at several selected narrow wavebands in the 3–5 or 8–12 $\mu$m IR spectral region at which gases (exhaust fumes, chemical agents, etc.) show characteristic "fingerprint" infrared absorption and emission lines. The sensor may use uncooled silicon micromachined IR detectors in a silicon vacuum package. The sensors and detectors may be any kind of technology. IR detectors are an illustrative example here. The estimated size, weight and power of a complete sensor (less downlink transmitter and battery) are 1 cc, 4 grams, 0.5 mW.

The sensor may be a multi-band IR sensor with a field of view directed upwards (dispersed or ground-based sensor) or downwards (MAV sensor) depending on the mission purpose. For exhaust gas detection, at least one IR band may be centered on the absorption line of a component of exhaust gas ($CO_2$, $H_2O$, CO, $NO_x$, depending on the engine and fuel type), and at least one IR band may be centered at a wavelength where these gases are transparent. The presence of exhaust gases may be indicated by an imbalance in the measured radiance at the two or more wavelengths. The imbalance may be produced by the different emissivity and temperature of exhaust gas components. For a downward looking MAV sensor, this imbalance may show a daily reversal of polarity, with crossover (minimum sensitivity) in the morning and evening.

The magnitude of the imbalance is difficult to predict analytically for a MAV downward looking sensor, since it may be strongly dependent on time of day, wind dispersal, etc., but may be easily measurable, since engines produce large volumes of exhaust gases (a 1000 cu inch engine produces about 100 liters per second at 1000 rpm idle).

An estimate of sensitivity may be more tractable for an upward looking sensor. It may be shown with calculations that hazardous chemical agents could be detected by an upward looking IR sensor. Such sensor may operate by sensing the radiance change caused by IR emission from the agent dispersed at altitudes where the air temperature is different from the apparent sky temperature. Using GB (Sarin), a particular chemical nerve agent, as an example, and assuming a local air temperature 1 degree C. different from the apparent sky temperature, C=10 mg/m3 of GB dispersed in a cloud L=10 m thick would produce an apparent temperature change of about 100 mK in a 20 cm−1 IR band centered at 1020 cm−1. The apparent sky temperature change induced in a nearby IR band where GB is transparent (1250 cm−1, 8.0 $\mu$m for example) is negligible in comparison. The IR signal from such a cloud of GB may therefore be detected (S/N≈5 for CL≈100 mg/m2) with a very low false alarm rate (about 2e−6) with an IR sensor with a noise equivalent target temperature difference (NETD) of 20 mK in a 20 cm−1 radiation bandwidth 1020 $cm^{-1}$. To cancel out variations in the sky temperature, the sensor would measure the fractional change in radiance with two IR sensors fitted with narrow-band IR transmission filters (e.g., for GB, 20 $cm^{-1}$ bands at 9.8 and 8.0 $\mu$m).

Figure 1B:
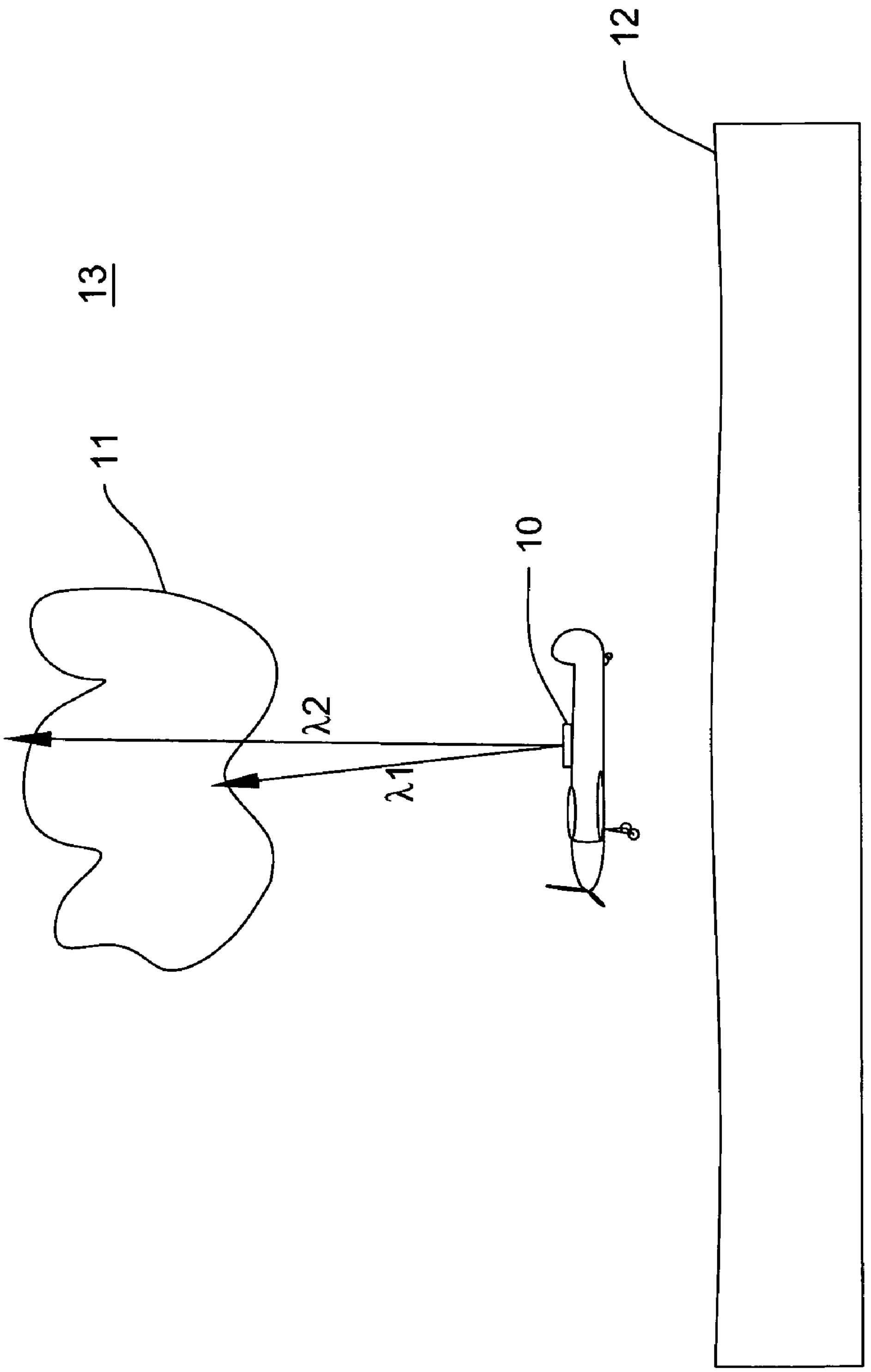
Figure 1C:
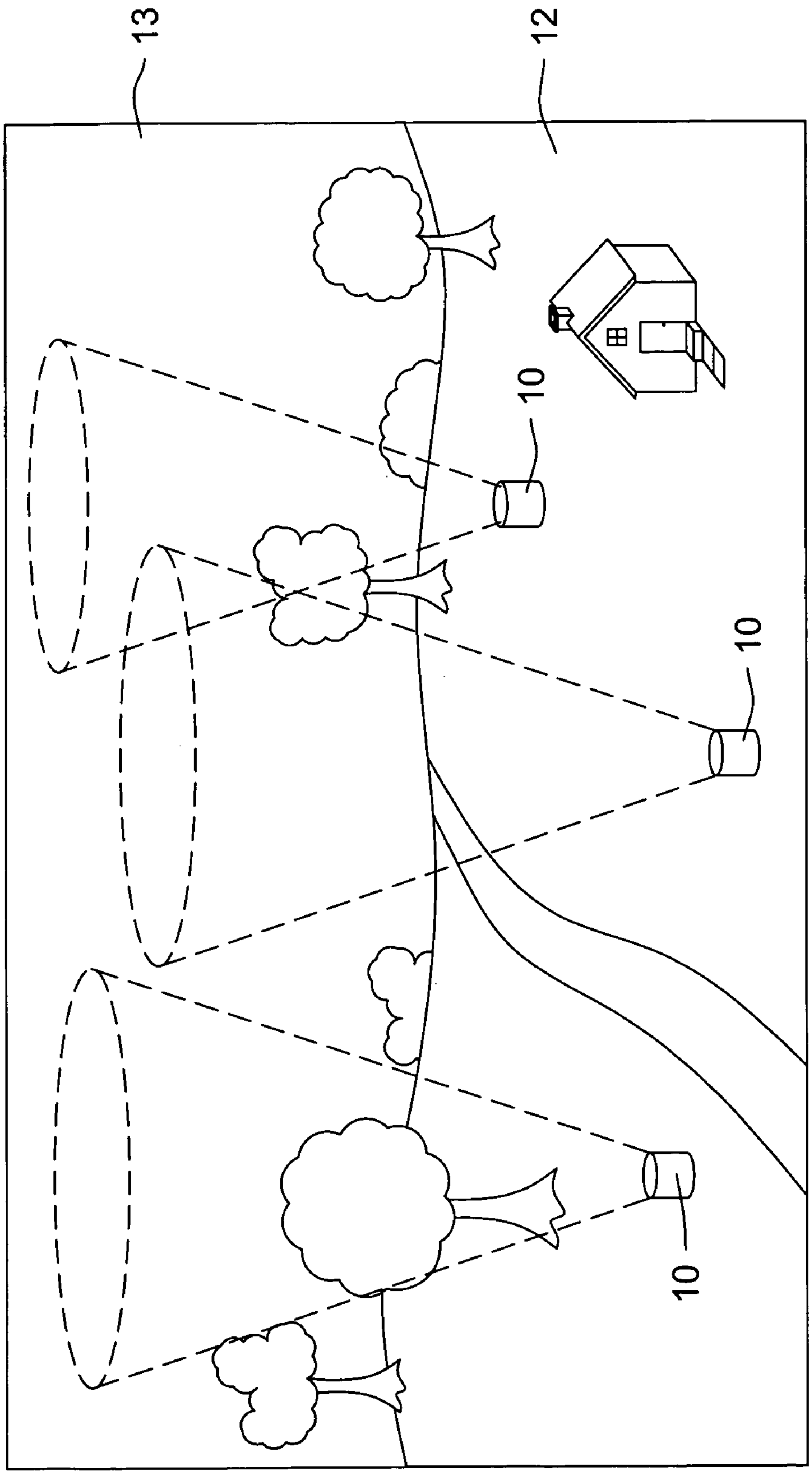
Figure 2:
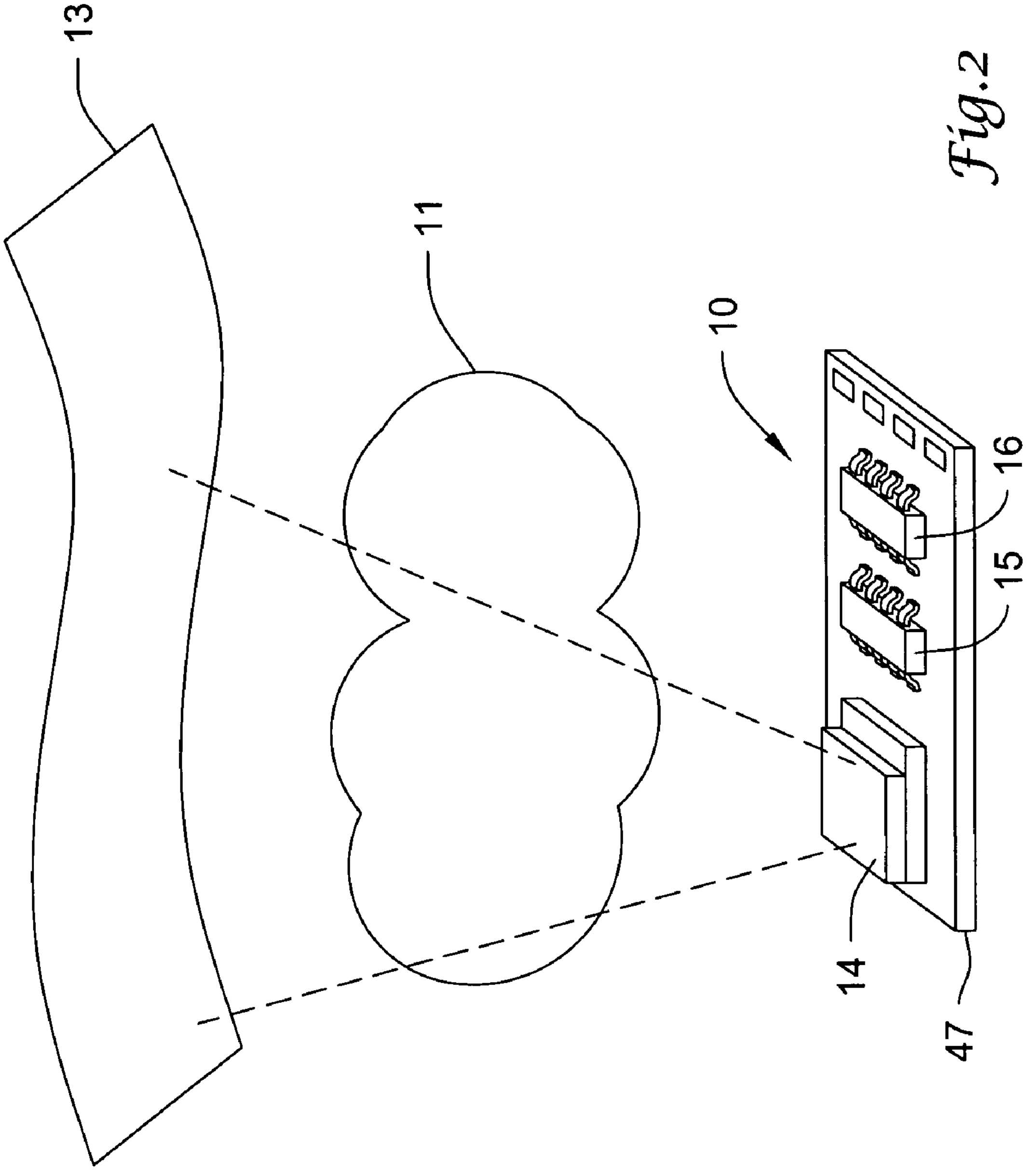
FIG. 2 shows the sensor relative to a gas cloud and the sky.
Figure 3:
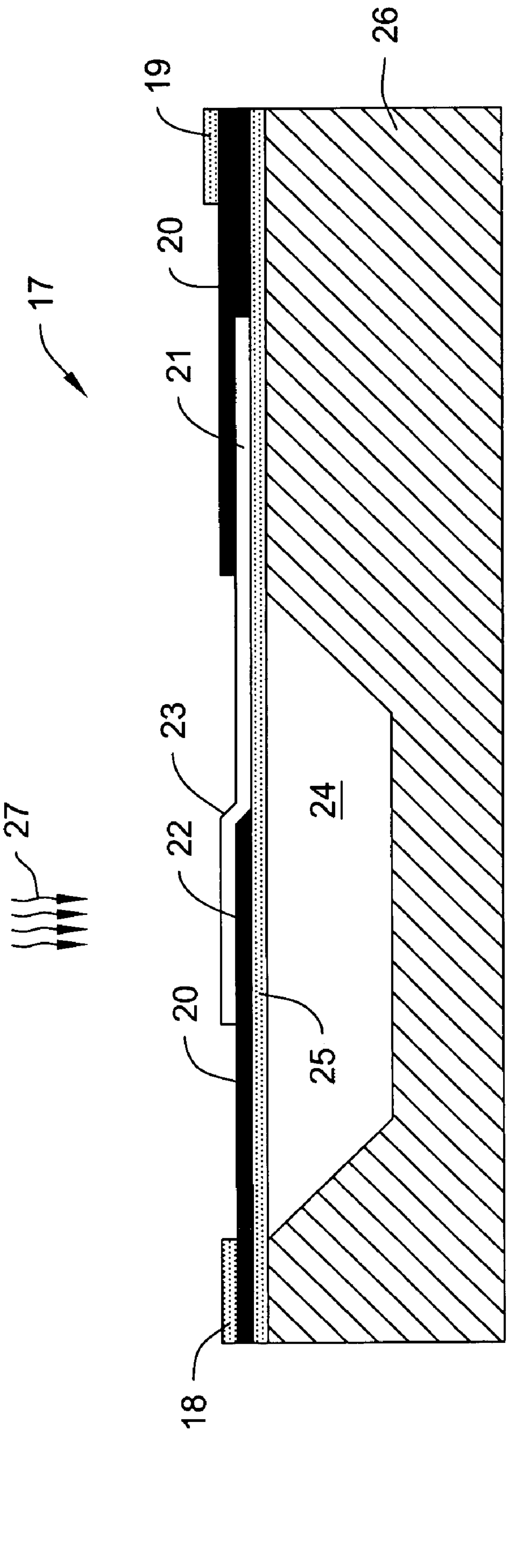
FIG. 3 illustrates a thermoelectric detector.

FIGS. 1*a* and 1*b* are illustrations of a downward-looking and an upward-looking sensor 10, respectively, with two IR detectors operating at narrow-band wavelengths λ1 and λ2, which sense the infrared radiance of a gas cloud 11 (λ1) and with a ground 12 or sky 13 background (λ2). FIG. 1*c* shows several upward-looking dispersed sensors 10 which may provide a protective surveillance of toxic agents for a specific area. FIG. 2 shows sensor 10 looking towards a warm gas cloud 11 being contrasted against a cold sky 13. Sensor 10 may have a multi-band IR array 14, amplifiers 15 and processor 16. More than two IR wavebands can be employed. An IR thermoelectric (TE) detector and an integrated vacuum package (IVP) may be applicable here. An illustrative example of such detector may be in U.S. Pat. No. 5,220,189, issued Jun. 15, 1993, with inventors Robert Higashi et al., and entitled "Micromechanical Thermoelectric Sensor Element", which is hereby incorporated by reference. An illustrative example of such package may be in U.S. Pat. No. 5,895,233, issued Apr. 20, 1999, with inventors Robert Higashi et al. and entitled Integrated Silicon Vacuum Micropackage for Infrared Devices", which is hereby incorporated by reference. The unit cell or detector of this sensor consists of a thin (8000 A) silicon nitride microbridge, typically 50 to 75 μm square, over a pit micromachined in the underlying silicon substrate. Microelectomechanical systems (MEMS) techniques may be utilized in the making or fabrication of the invention. Information about MEMS may be provided in U.S. Pat. No. 6,277,666, issued Aug. 21, 2001, with inventors Kenneth Hays et al. and entitled "Precisely Defined Microelectromechanical Structures and Associated Fabrication Methods", which is hereby incorporated by reference. The sensors may operate by a thermal detection mechanism, i.e., incident IR radiation may heat the microbridge. Thin (1000 Å) thermoelectric metal films may form a thermocouple-pair and generate a direct voltage signal. Sensor 10 may be 'self zeroing' at any temperature, and hence may not require a temperature stabilizer or high-bit A/D. FIG. 3 shows a cross-section of a TE detector 17. It may have electrical contacts 18 and 19 situated on a metal 20, a cold TE junction 21 and a hot TE junction 22 of metals 20 and 23. Junction 22 is supported over an etched pit or well 24 by a silicon nitride bridge 25. All of this may be formed in and supported by a substrate 26. IR radiation 27 may impinge detector 17 which in response an electrical signal noting the impingement appears at contacts 18 and 19.

Figure 4A:
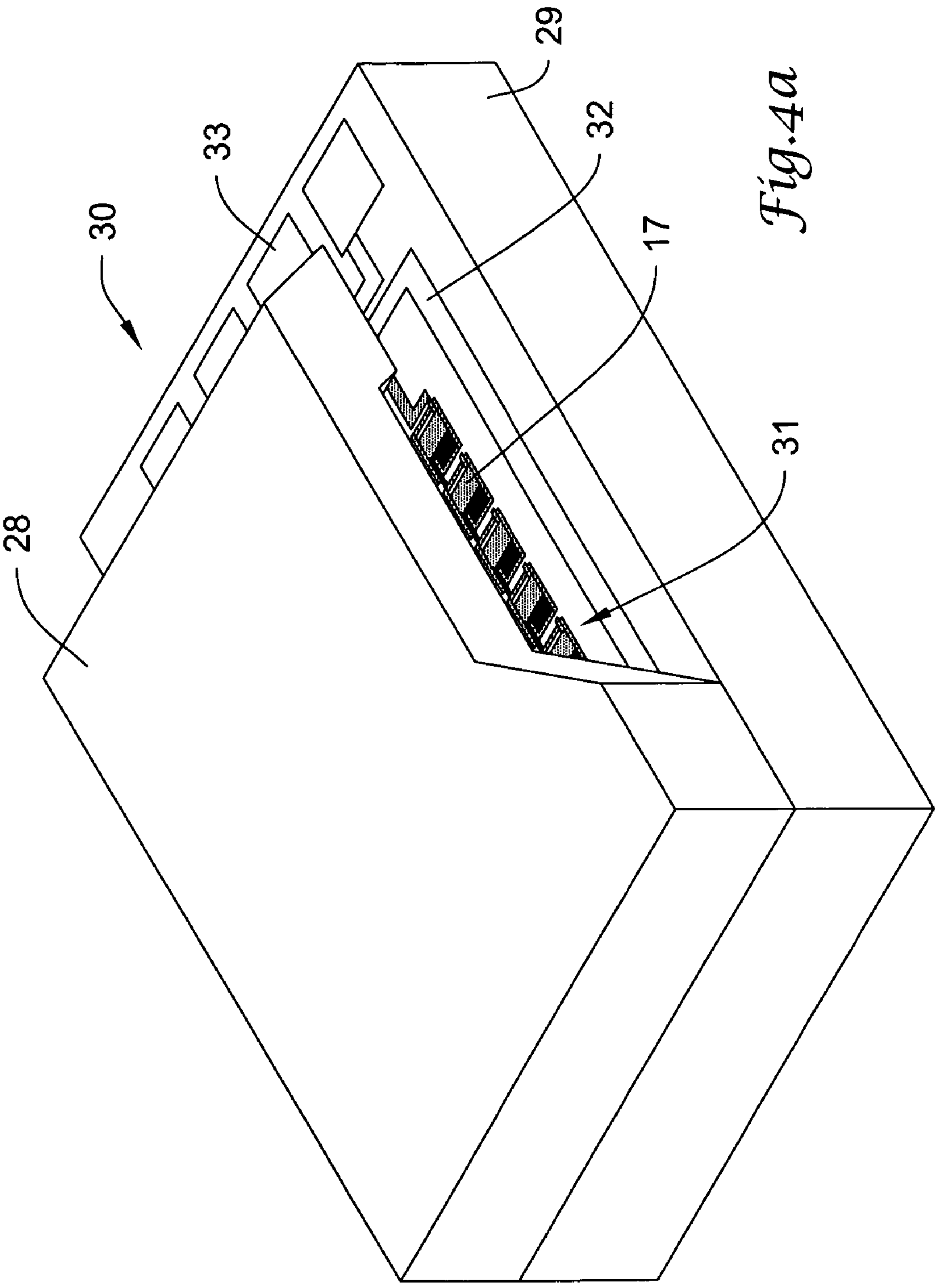
FIGS. 4*a* and 4*b* reveal the sensor in conjunction with a vacuum package.
Figure 4B:
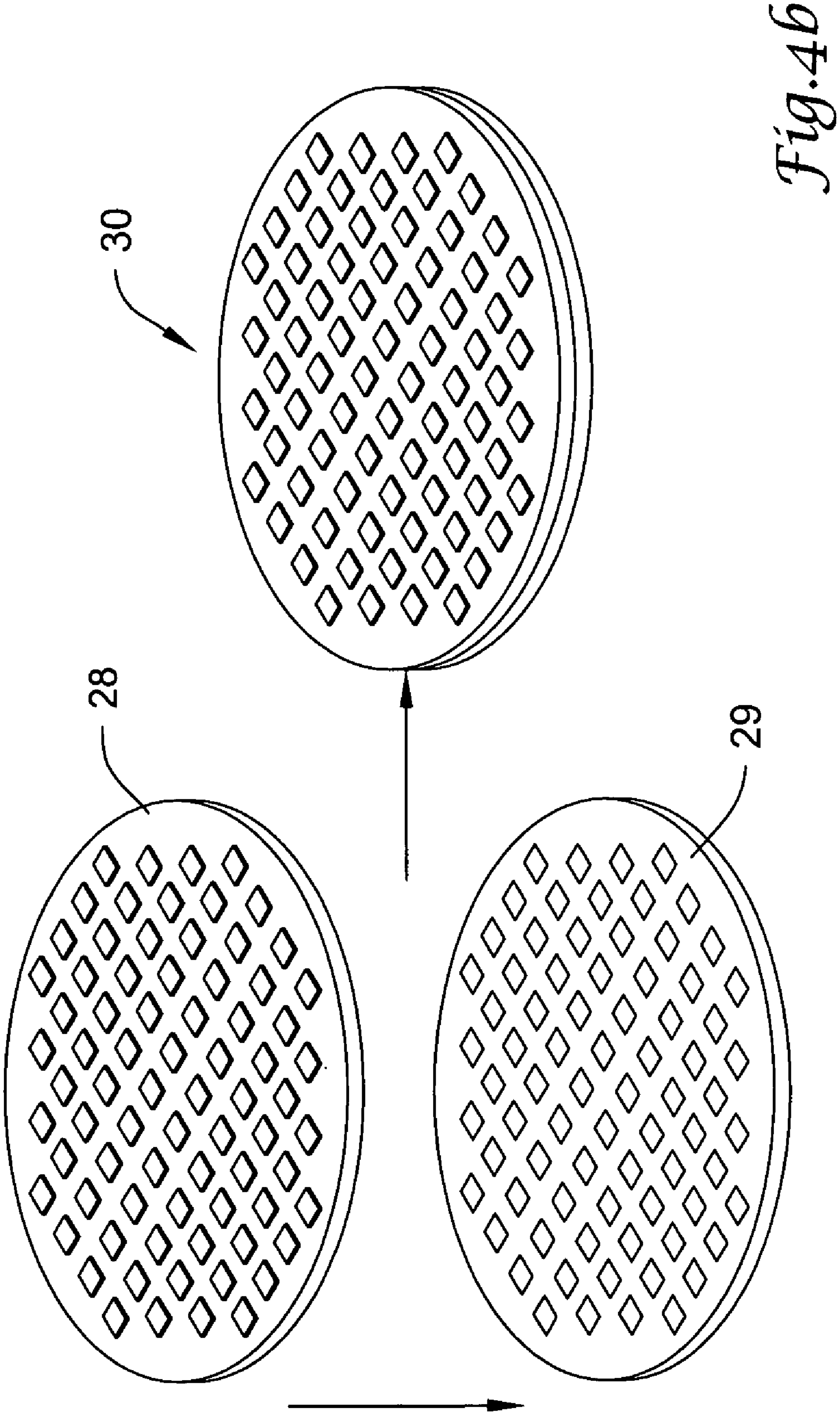

TE detectors 17 or sensors should operate in a vacuum to achieve full sensitivity (as any gas pressure more than 75 mTorr may dampen the thermal signals unacceptably). One may use a low-cost light-weight wafer-scale vacuum encapsulation using an IR-transparent silicon "topcap" 28 on a substrate 29 as shown in FIG. 4*a*. FIG. 4*b* illustrates the basic fabrication of wafer-to-wafer bonding of topcat wafer 28 to device wafer 29 to produce a low-cost vacuum package 30. Topcap 28 may be an anti-reflective coated silicon window. Item 30 is regarded as an integrated vacuum package (IVP). Between topcap 28 and substrate 29 is a cavity 31 that contains detectors 17. There is a seal ring 32 for wafer-to-wafer sealing of cavity 31 between topcap 28 and substrate 29. Gold pads 31 are for wire bonding the connections to detectors 17. Cavity 31 may be evacuated via a port through the back of substrate or wafer 29. This low-cost vacuum encapsulation adds negligible weight (i.e., about 0.02 grams) to detector array 14. A hermetically sealed 30×30 mosaic IVP TE sensor may have an overall die size of about 5 mm×5 mm.

For this non-imaging application, a 2D array is not required, but for adequate sensitivity it is necessary to use a mosaic of many individual TE detectors 17, electrically interconnected, to form a larger-area "mosaic" TE IR sensor 10, because the NETD improves as the square root of the mosaic area. Thus, a 30×30 mosaic is 30 times more sensitive than one unit cell 17, and can provide very good performance even with narrow radiation bandwidth. IVP sensors 14 have long vacuum lifetimes (over 10 years), operate up to 180° C., and can be easily handled like conventional silicon electronic chips. These IR sensors may be produced in volume production (i.e., thousands) at very little cost each.

Figure 5:
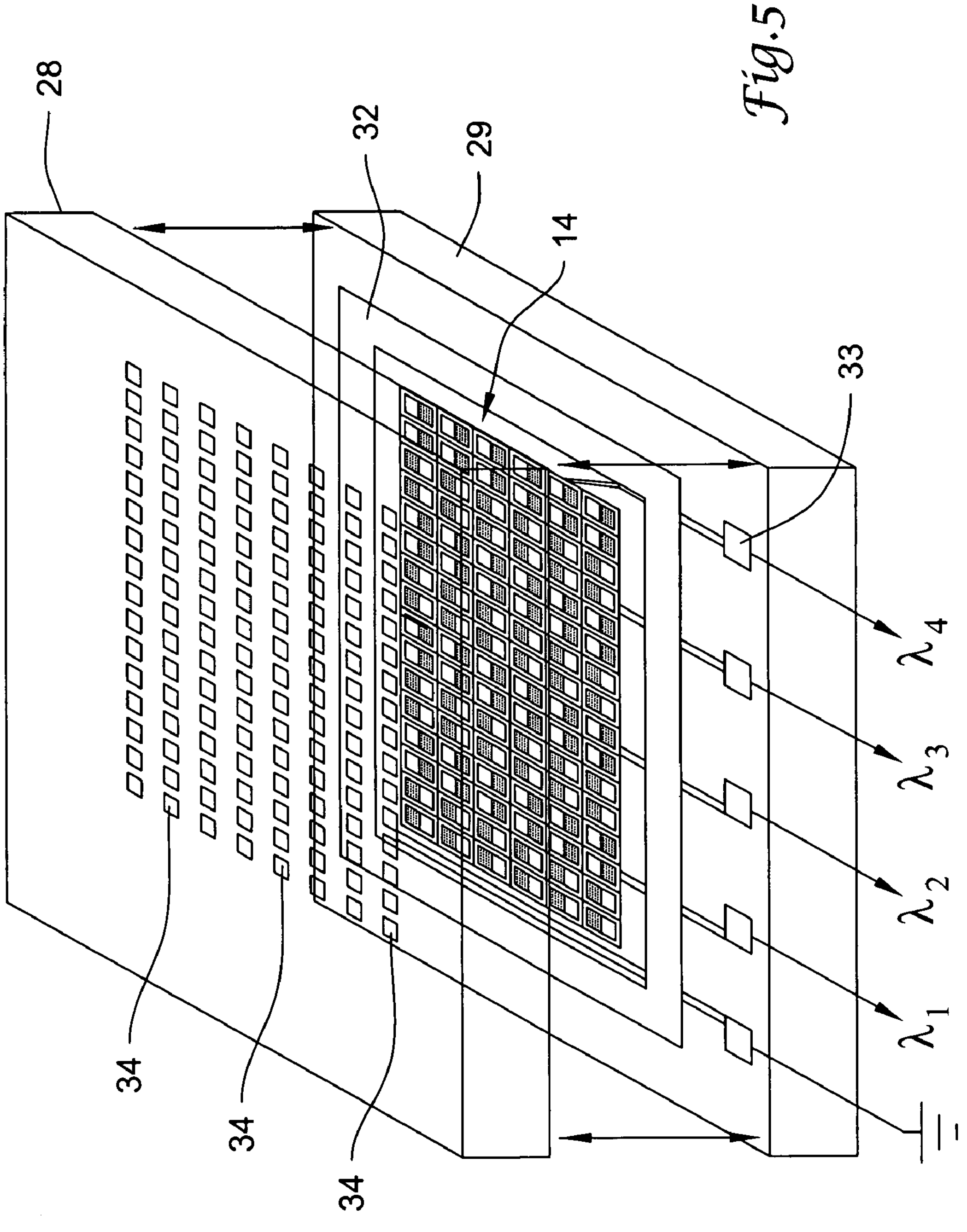
FIG. 5 is a layout of the detectors and filters of the sensor.
Figure 6:
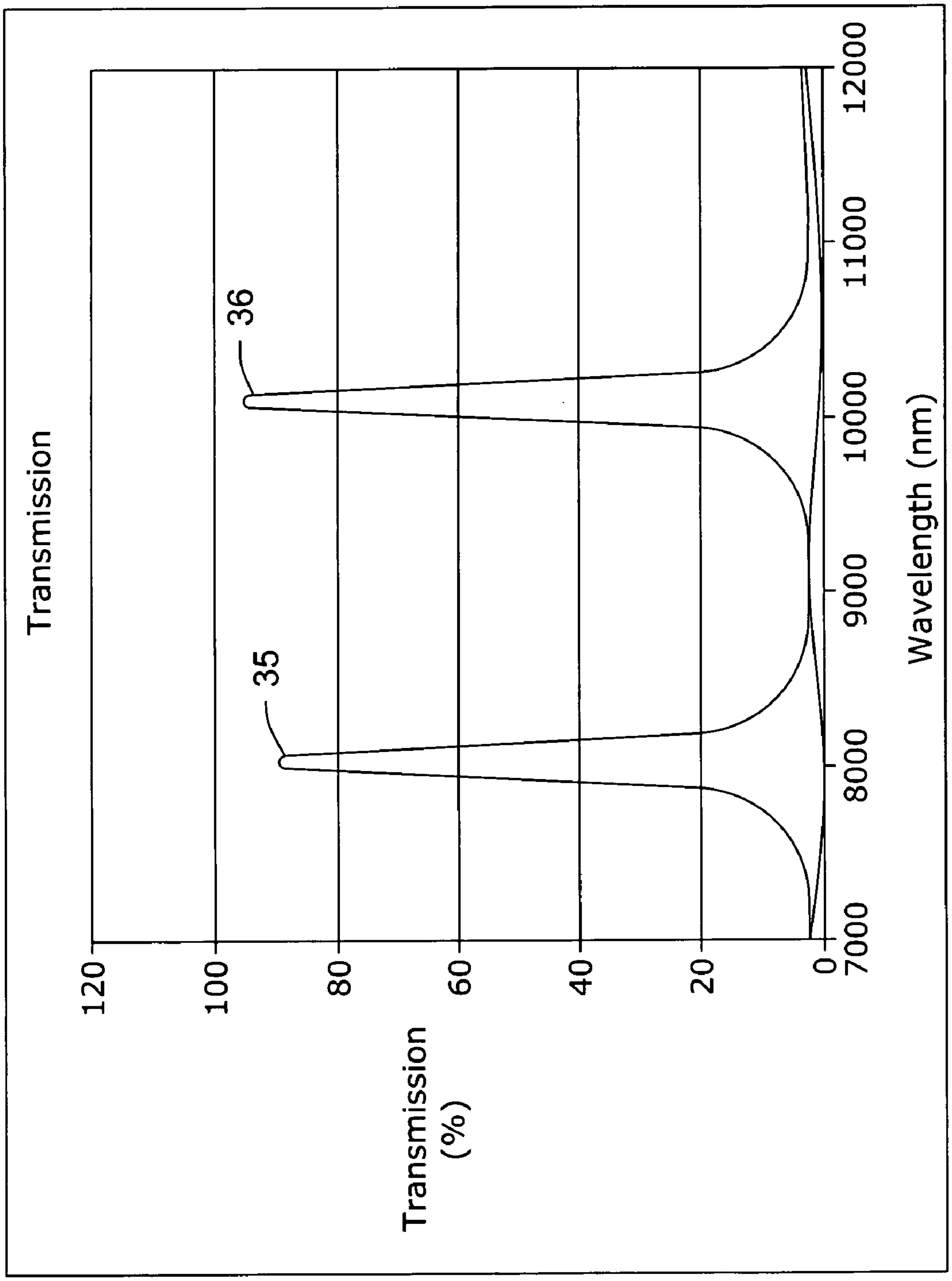
FIG. 6 is a graph showing transmission peaks of two thin-film interference filters.

FIG. 5 shows sensor 10 having multi-band capability utilizing a mosaic of IR bandpass filters. The multi-band capability of IR detectors 17 may be provided by fabricating narrow-band interference filters 34 directly on the inner surface of the IVP topcap 28 using a photolithographic process to generate alternating IR transmission bandpass filters with 75 μm periodicity, matching the 75 μm periodicity of the underlying TE detectors 17. A very simple dielectric stack may be employed to produce the selected IR bandpass filters. FIG. 6 reveals a calculated transmission of two thin-film interference filters (8 layers of Si and $SiO_2$) with transmission peaks 35 and 36 at 8 μm and 10 μm, respectively (20 $cm^{-1}$ corresponds to about 200 nm wavelength width).

Figure 7:
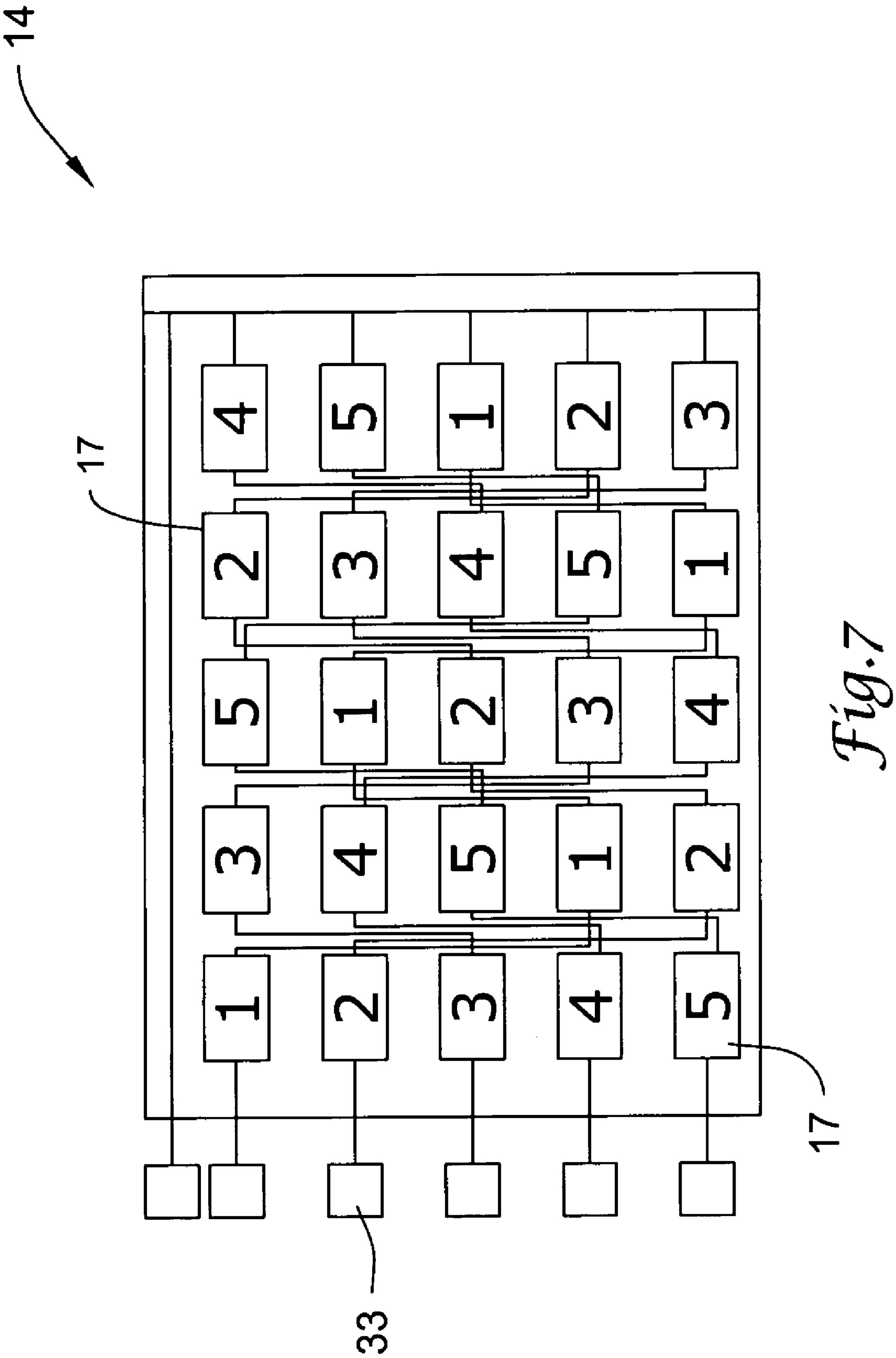
FIG. 7 is a layout of detectors and their connections into groups.

For a dual-band sensor, alternate TE detectors may be electrically interconnected in series and/or parallel, so that sensor 10 may automatically produce separate electrical signal voltages for each IR waveband, with approximately equivalent, about the same or essentially identical fields of view. A detector 17 near the edge of array 14 on substrate 29 may have a different field of view than a detector 17 in the center of array 14 because the side or edge of topcap 28 may obstruct part of the view from the outside to the detector 17 near the edge, whereas such obstruction would not be present for detector 17 in the center. There may be a number of detectors of the same wavelength in the array which make up a group of detectors 17. Detectors 17 of the same group and wavelength may be connected together with series or parallel electrical connections or a combination of such connections. The distribution of the detectors for the various wavelengths may be such that the group has a cumulative, composite, average or resultant field of view representative of the group's constituent detectors 17. The result is that the fields of view of the groups may be essentially the same or equivalent. FIG. 7 shows an example of five groups of detectors 17, one group for each wavelength or "color". Detectors 17 labeled "I" are of group 1, labeled "2" are of group 2, and so on. The colors (i.e., various wavelengths) can be distributed according to a regular pattern, which probably may be designed differently for different numbers of colors, but the general principle is the same. The various "colored" detectors 17 comprising the mosaic are distributed across the mosaic area, so that each individual "color" detector 17 has a substantially-equal number of near neighbors of each of the other "colors". All individual detectors of each separate color are electrically connected together (either in series, parallel or a combination thereof) to give a single output signal of that "color" and incorporating a field of view for the respective group. There may be a case in which the colors are distributed randomly, which achieves substantially the same equalization of the fields of view among the groups, even though a regular pattern is not used. Various "colored" detectors 17 comprising the mosaic may be distributed randomly across the mosaic area, so that each individual "color" detector 17 has, on the average, a substantially-equal number of near neighbors of each of the other "colors". All individual detectors 17 of each separate color may be electrically connected together (either in series or parallel, but usually in series) to give a single output signal of that "color". The random configuration may work better when the number of detectors in array 14 is large (i.e., greater than 50).

Figure 8:
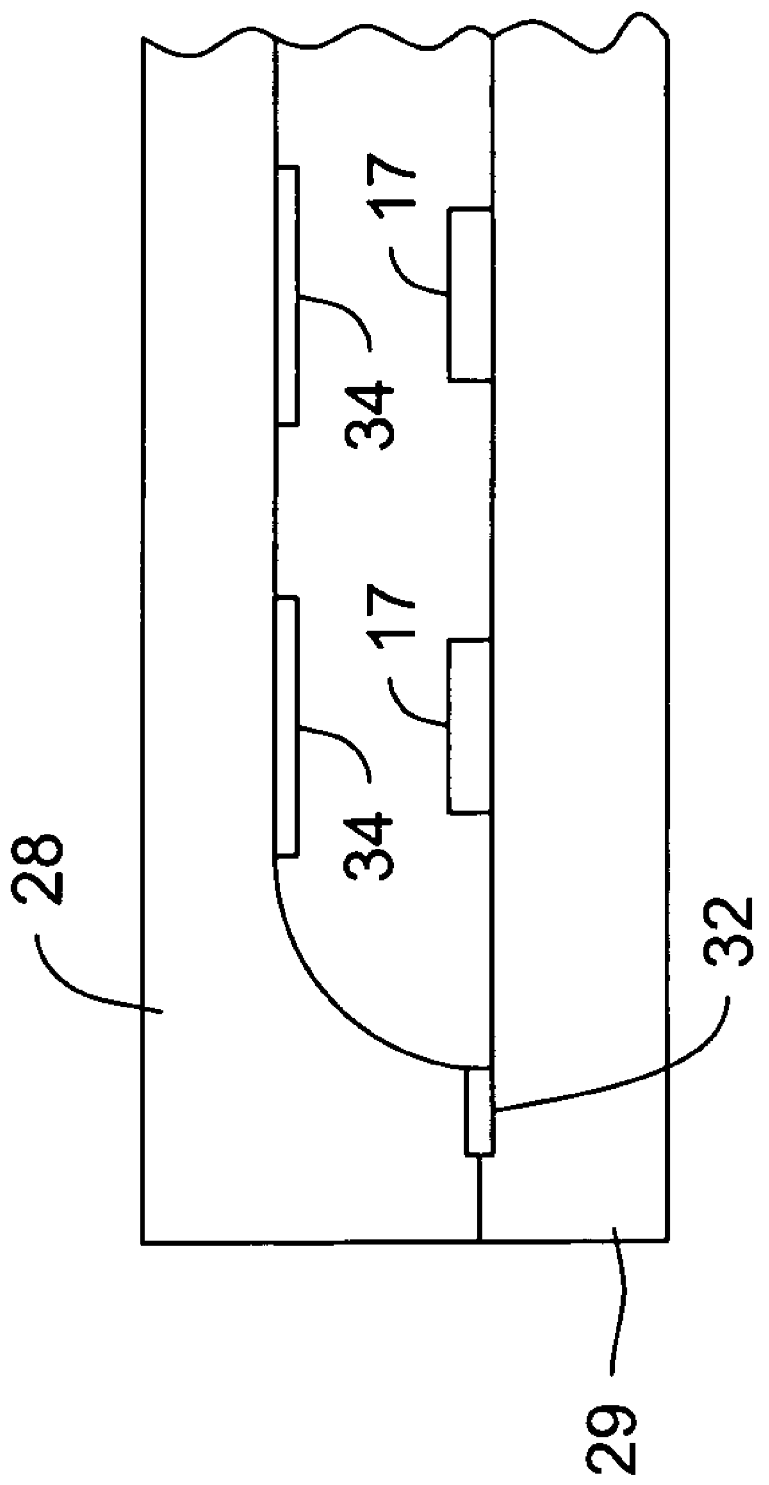
FIG. 8 is a side view of several detectors and their corresponding filters.

The wavelength or "color" of a detector 17 may be determined by the filter 34 situated between the sensing surface or junction of detector 17 and that which is observed. FIG. 5 reveals a perspective of filters 34 relative to detectors 17. Filters 34 designate the "colors" for detectors 17. The filters 34 are laid out according to groups as described above. FIG. 8 is a side view of the relationship of filter 34 to detector 17. Filters 34 may be put on the inside surface of topcap 28 with photolithographic processes.

The advantages of TE infrared thermal detectors 17 in the present sensor 10 include Low cost (because of the use of commercial silicon fabrication and vacuum package process), robustness (>12,000-g's, 180° C. tolerant, and European Space Agency space-qualified), suitability for long integration times (un-measurable 1/f sensor noise), high sensitivity (NETD<10 mK with 20 cm−1 IR bandwidth), broadband responsivity (<3 to >15 μm), and ease of operation (uncooled, no thermal stabilization or bias voltage required, direct dc signal voltage). Sensor 10 may utilize other kinds of detectors 17.

The NETD of a 2.5 mm square 30×30 mosaic IVP TE sensor 10 may be calculated to be <10 mK in the operating mode of the program with 10 seconds integration time, 20 $cm^{-1}$ waveband near 10 μm, 290K target temperature, and F/1 optical aperture. The NESR may be computed to be 5.4e−10 W/cm2·sr·cm−1. Two such IR detectors 17 may be placed side by side, viewing the sky via two IR thin-film multilayer filters 34 centered at (in the case of GB) 9.8 μm and 8.0 μm, to give a good signal/noise ratio (10:1 for CL=100 mg/m2) for GB under most atmospheric conditions.

Figure 9:
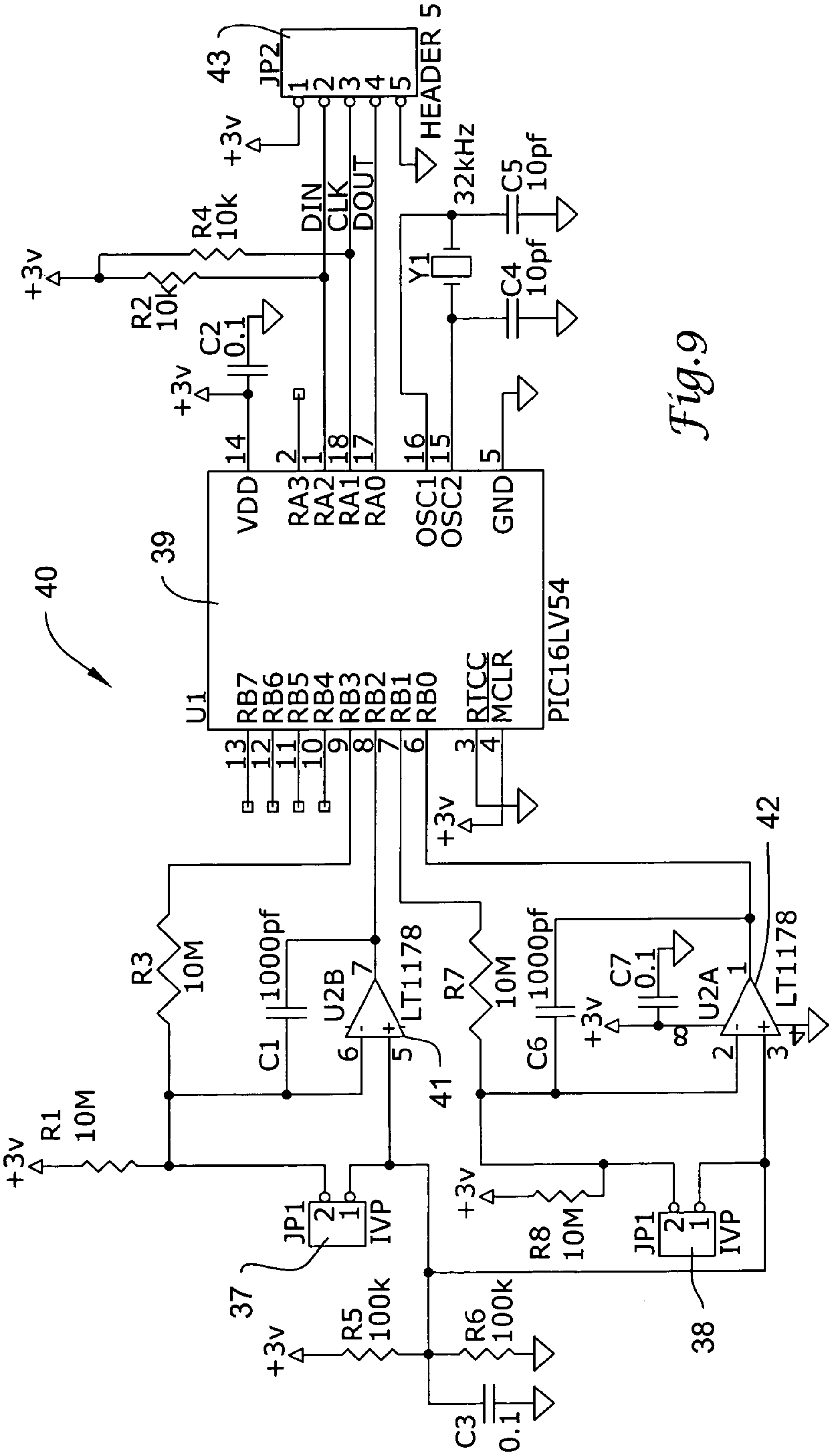
FIG. 9 is a schematic of some electronics for the sensor.

Sensor 10 electronics may include a CMOS electronic circuit 40 as shown in FIG. 9 may be used to compute the IR ratio signal of a background signal and a gas detection signal from corresponding detectors 17 to inputs 37 and 38, respectively. IR detector signals pass through preamplifiers 41 and 42 and are digitized with a microprocessor 39 operating in a sigma-delta feedback loop. The ratio signal may be accessed at output 43. An RF link may be connected to output 43. Circuit 40 uses 150 μA at 3V (0.5 mW).

Figure 10A:
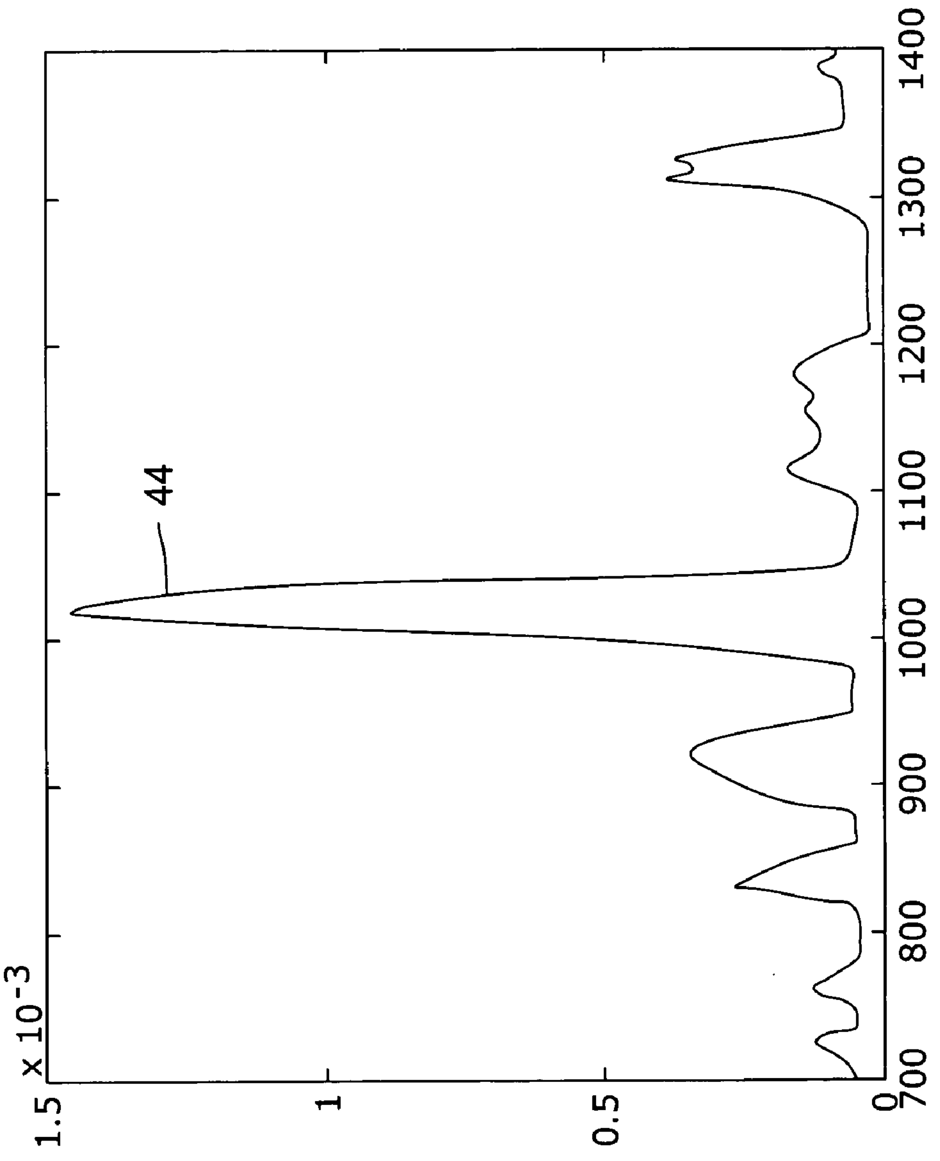
FIGS. 10*a*, 10*b* and 10*c* show absorptivity coefficients of an agent and two interferents.
Figure 10B:
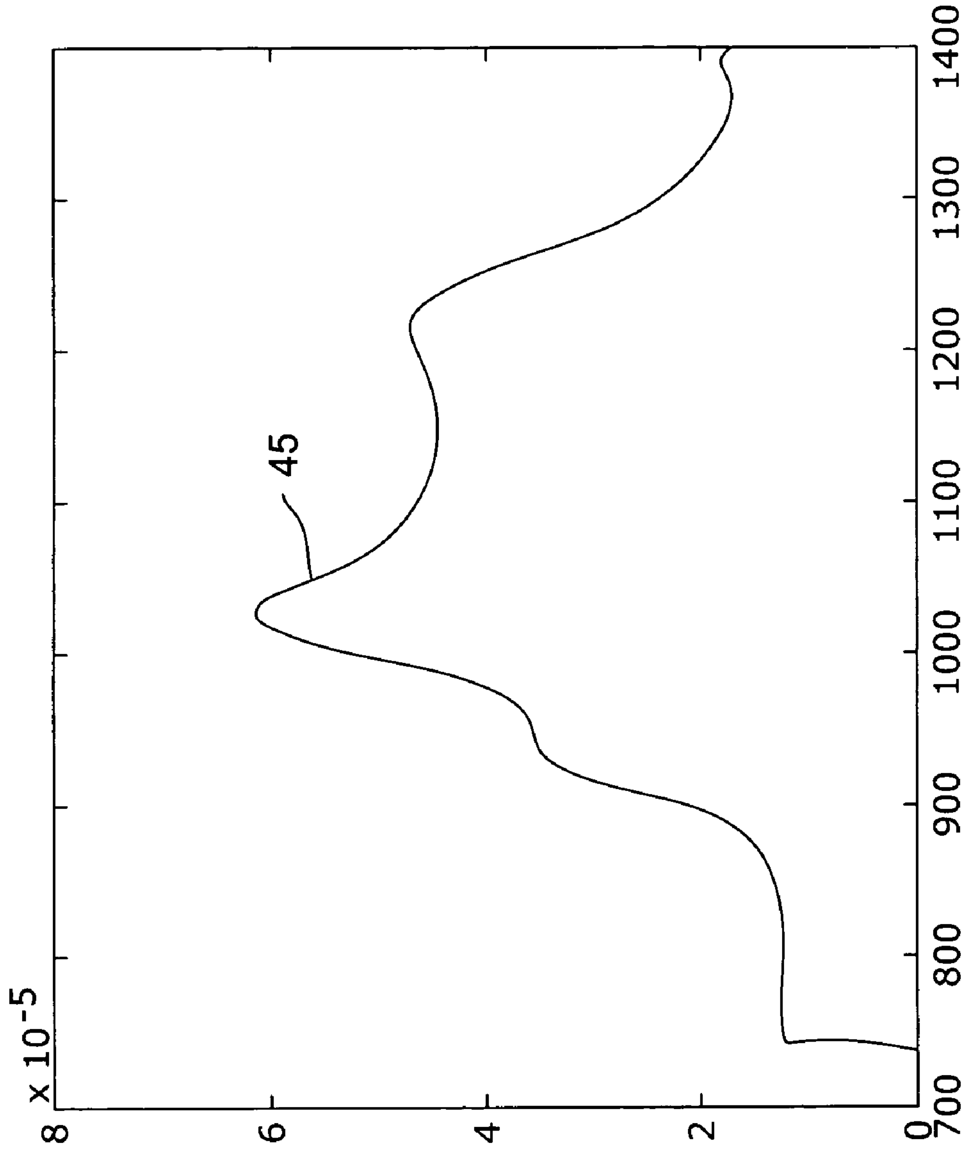
Figure 10C:
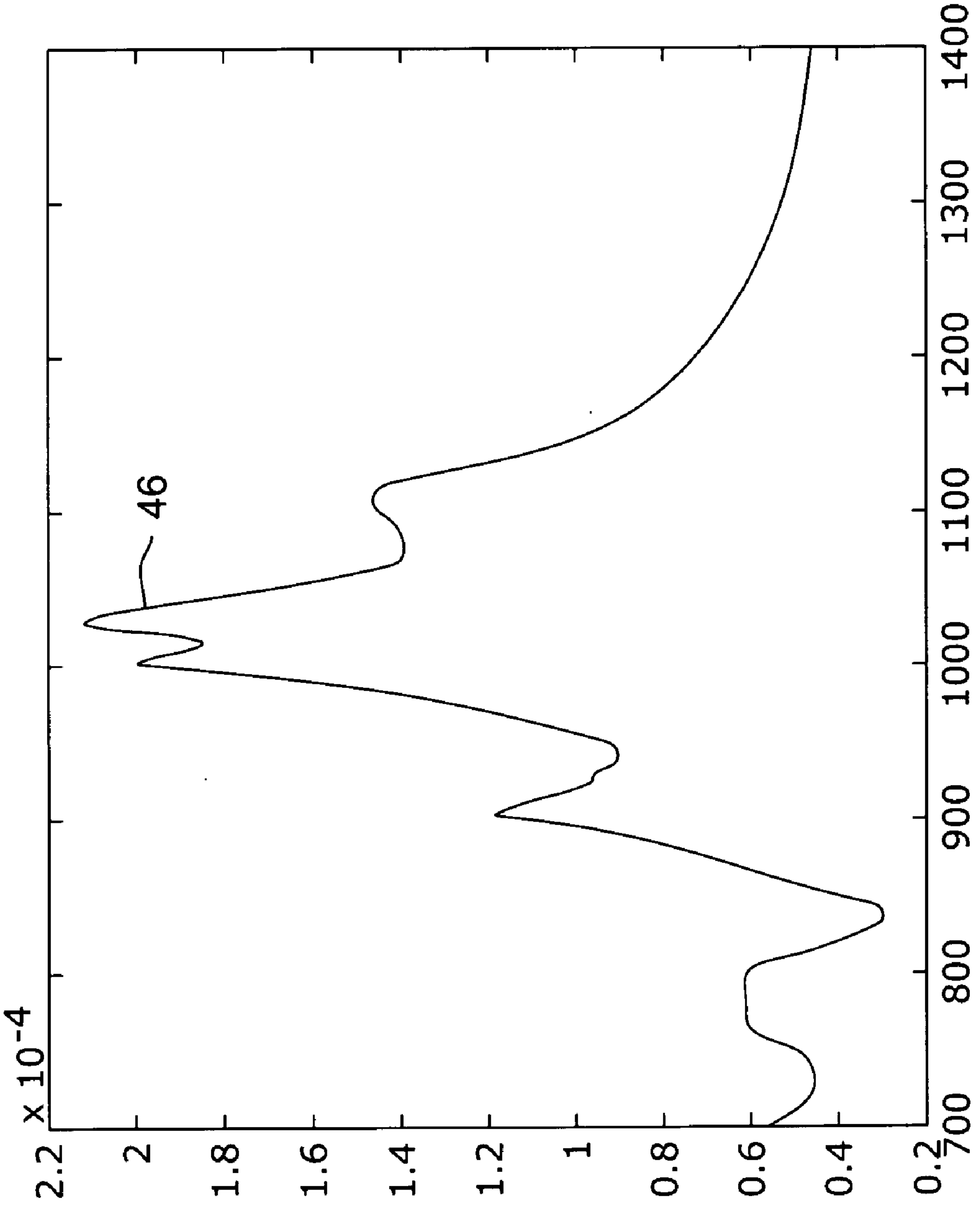

Discrimination between chemical agents and interferents may be detected. The military M21 remote sensing chemical agent alarm and joint service lightweight standoff chemical agent detector (JSLSCAD), which are remote chemical agent sensors, measure the radiance at multiple narrow wavebands within the range 800 to 1200 wavenumbers, where atmospheric transmission is normally good (except for the ozone doublet near 1030 cm−1) and chemical agents have distinctive spectral characteristics. Curves 44, 45 and 46 in FIGS. 10*a*, 10*b* and 10*c* show the absorptivity coefficients of chemical nerve agent GB, and two common battlefield interferents, white phosphorus (WP) smoke and Fort Benning dust (dust) near 10 μm wavelength, respectively.

In order to differentiate chemical agents from each other, and from interferents, at least two, and possibly many, different IR wavebands must be measured. For example, looking at FIGS. 10*a*, 10*b* and 10*c*, the relative fractional radiance change at 8.0 μm (1250 $cm^{-1}$) compared to 9.8 μm (1020 $cm^{-1}$) appears small for GB, but significant for either WP or dust. The spectral resolution that has been used (with M21 and JSLSCAD) to detect and differentiate chemical agents against complex background IR signatures may be 4 wavenumbers. This however may require 100 IR measurement bands to cover the full 8–12 μm spectral range, which seems not conducive to a low-cost sensor. Fortunately, the skyward viewing geometry of the proposed sensor greatly simplifies the background IR signature, so that a fewer number of wider spectral bands may be used. Since the minimum practical number, and width, of the wavebands for reliable species identification may need to be determined, one could analytically determine how a variation in the number of IR bands and bandwidths affect the ability of the proposed sensor to discriminate chemical agents from harmless atmospheric contaminants (dust, smoke, etc.) and discriminate different classes and types of chemical agents from each other. One may use IR spectra. One may take into account recent improvements in signal processing and pattern recognition techniques (autoregressive (AR) modeling, Markov Random Field (MRF) and neutral net processing. One may select the smallest number of IR bands, with the widest wavebands, that may produce a useful practical result in sensor 10. The results may be used to determine the optimum number of IR bands and bandwidths required in a production sensor.

A look at this has been performed, using JSLSCAD data as a baseline. This is tended to indicate that higher-resolution is more important than the number of bands employed. Adequate performance may be attained with five to eight wavebands, with full width half maximum (FWHM) of 16 $cm^{-1}$ (approx 0.2 μm). Suitable center-wavebands for various agents are indicated as follows: GA, 1046 cm−1; GB, 1026 cm−1; GD, 1022 cm−1; GF, 1016 cm−1; VX, 1038 cm−1; HD, 1231 cm−1; HN3, 1121 cm−1; and Lewisite, 814 cm−1.

An 8–12 μm sensor 10 may be fabricated using circuit 40 of FIG. 9. Sensor 10 may use one 45 degree field of view (FOV) 30×30 mosaic IVP TE IR sensor on one channel, with the other channel being used to measure air temperature with a thermistor. This may be a dual-band IVP TE sensor 10 calibrated radiometer. The 30×30 mosaic TE IVP sensor 10 may be placed in a circular aluminum optical shroud on a circuit board. Two chips, amplifiers 15 (41, 42) and microprocessor 16 (39), and array 14 may be placed on circuit board 47.

Figure 11:
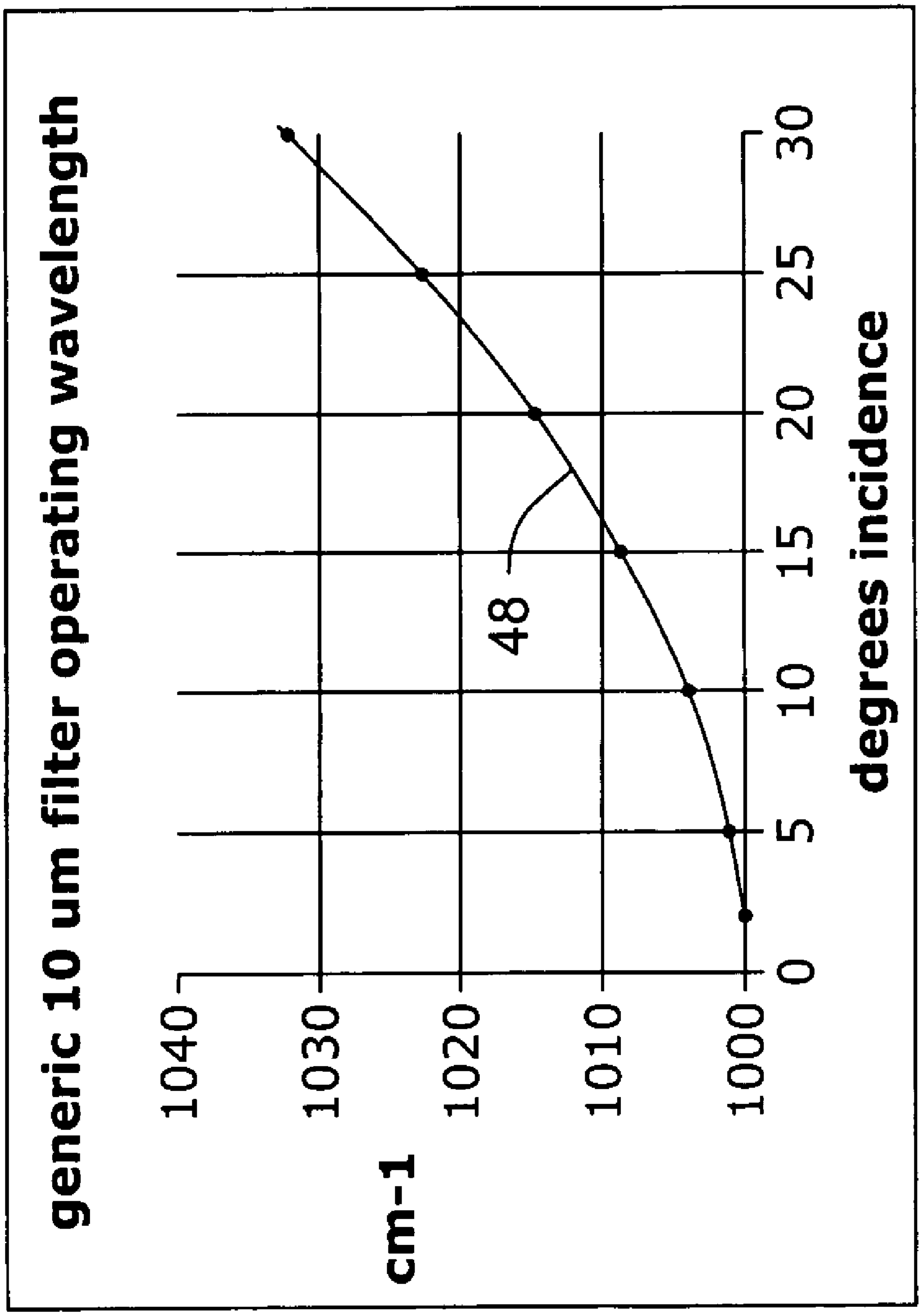
FIG. 11 shows the effect of variation of an angle of incidence on a narrow-band filter.

For the lowest cost and weight, sensor 10 may use no lens and rely on the overhead chemical agent filling the vertical field of view (FOV). If no lens is used, then incident rays from the sky within the FOV may pass through the narrow-band IR filters at varying angles of incidence. In this case, one may consider the change in IR filter characteristics with angle of incidence. The computed change in center wavelength of a 10 μm bandpass filter as a function of angle of incidence of the radiation shows that plus/minus 25 degrees (i.e., about F/1) may be acceptable, so no collimating lens should be required for 20 cm−1 wavebands and F/1 FOV. A germanium window may be used to provide environmental protection. The window may be made optically diffusing, to provide more uniform fields of view to IR detectors 17. Curve 48 of FIG. 11 shows the effect of variation of an angle of incidence on a generic narrow-band filter centered at 1000 cm−1 (10 μm wavelength).

Figure 12:
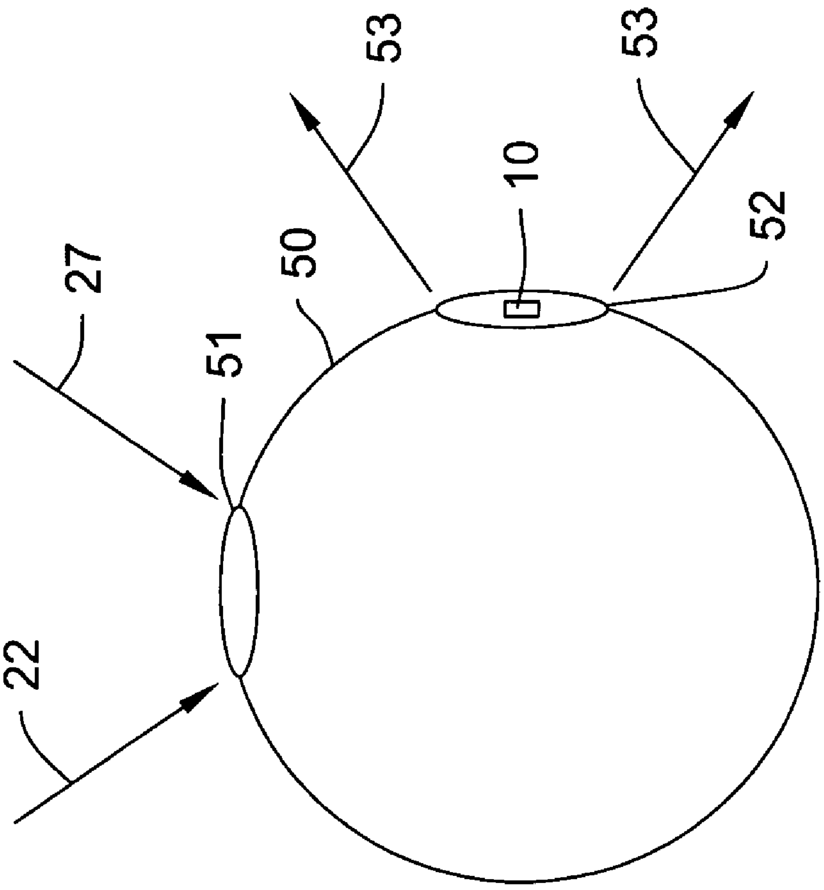
FIG. 12 reveals a light integrating sphere.

It is significant that the fields of view of the groups of detectors 17 for the different IR bands be essentially identical, so that point objects (dust specs, isolated clouds, etc.) do not affect one band more than another. This may be substantially achieved by the use of a mosaic of IR detector 17 and IR filters 34, with every detector operating in one band being surrounded by other sensors operating in the different bands, as described above. Impinging radiation 27 field can also be substantially randomized by the use of an "integrating sphere" 50 as shown in FIG. 12. Radiation 27 may enter a portal 51 of sphere 50. Radiation 27 is reflected around internally in sphere 50 by the reflective inside surface of sphere 50. Randomized radiation 53 may exit from sphere 50 through portal 52. However, sensor 10 may be placed at the portal 52 exit of sphere 50 to detect the radiation.

Sensor 10 has high shock tolerance. IR detectors 17 have been tested to 14,000 g, and may tolerate more than 20,000 g. Electronic circuits may be hardened to 20,000 g by encapsulation in supporting media. Lens components might be able to tolerate 20,000 g with suitable robust mounts.

Weight, size and power of sensor 10 may be favorable for many users. Using the known density of materials, one may estimate the weight of the expected components of chemical agent sensor 10. A single band sensor 10 is reviewed in the weight calculation table 54 in FIG. 13. Additional infrared bands may be added with little additional impact in size/weight/power/cost.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A sensor comprising:

a plurality of groups of detectors situated on a support structure; and wherein:

each detector of said plurality of groups of detectors has a field of view;

at least one field of view is different from another field of view;

the detectors of each group of detectors are connected resulting in a field of view of the group of detectors; and the fields of view of the groups of detectors are about the same.

2. The sensor of claim 1, wherein:

the detectors of a group are sensitive to the same bandwidth;

each group of detectors is sensitive to a bandwidth that is different from a bandwidth to which another group of detectors is sensitive.

3. The sensor of claim 2, wherein:

a group of detectors has a bandwidth where substances subject to detection are transparent; and at least some of the groups of detectors have bandwidths centered on absorption lines of the substances subject to detection.

4. The sensor of claim 3, wherein:

an imbalance, between an amount of radiance detected by the group of detectors having the bandwidth where the substances subject to detection are transparent and radiance detected by a group of detectors having a bandwidth centered on an absorption line of a substance subject to detection, indicates a presence of the substance.

5. The sensor of claim 4, further comprising a filter situated proximately on each detector wherein the filter determines the bandwidth of detection of the respective detectors.

6. The sensor of claim 5, further comprising a topcap situated on the support structure, wherein said topcap and support structure result in an integrated vacuum package enclosing said plurality of groups of detectors.

7. The sensor of claim 6, wherein each said filter situated proximately on each detector is situated in the topcap.

8. The sensor of claim 7, wherein each detector is sensitive to infrared radiation.

9. The sensor of claim 8, wherein the fields of view of the groups of detectors are directed in a pre-determined direction.

10. The sensor of claim 9, wherein the sensor is made with microelectromechanical systems (MEMS) techniques.

11. The sensor of claim 9, further comprising a sphere wherein the sphere comprises:

a first port; and a second port; and wherein:

the sphere is hollow having a reflective inner surface;

the plurality of groups of detectors situated on the support structure is situated at the second port with the fields of view directed towards the inner surface of the sphere; and the second port of the sphere has a field of view directed out from the sphere.

12. A sensor comprising:

an array of at least two groups of detectors; and wherein:

each detector of the at least two groups of detectors has a field of view, wherein at least one field of view is different from another field of view;

each group of detectors has a primary sensitivity to a bandwidth of radiation that is different from a bandwidth of radiation that another group has sensitivity to;

the detectors of each group of detectors are connected with one another but not with any detector of another group of detectors;

each group of detectors has an output connection;

each group of detectors has a cumulative field of view; and the detectors of the at least two groups of detectors are situated in said array to result in the cumulative fields of view being essentially equivalent to one another.

13. The sensor of claim 12, wherein the detectors of the at least two groups are randomly situated in locations of said array.

14. The sensor of claim 12, wherein each detector of the at least two groups is situated so as to be next to about the same number of detectors of the other groups.

15. The sensor of claim 12, wherein said array is enclosed within a sealed package.

16. The sensor of claim 15, wherein the primary sensitivity to a bandwidth of radiation of each group of detectors is provided by a filter proximate to each detector of the at least two groups of detectors.

17. The sensor of claim 16, wherein each filter proximate to each detector is situated in a portion of the sealed package.

18. The sensor of claim 17, wherein:

a group of detectors has a first bandwidth centered on an absorption line of a fluid subject to detection; and the fluid subject to detection is transparent to detection by a group of detectors having a second bandwidth.

19. The sensor of claim 18, wherein:

an output connection of the group of detectors having the first bandwidth is connected to a processor;

an output connection of the group of detectors having the second bandwidth is connected to the processor; and the processor outputs a signal indicative of a relativeness of a signal from the output connection of the group of detectors having the first bandwidth with a signal from the output connection of the group of detectors having the second bandwidth.

20. The sensor of claim 19, wherein the signal indicative of the relativeness provides information about detection of a fluid.

21. The sensor of claim 20, wherein the detectors are infrared radiation detectors.

22. A sensor comprising:

a plurality of groups of detectors; and wherein:

each detector has a field of view, situated on a structure;

at least on field of view of a detector is different from another field of view of another detector, due to the structure;

the detectors of each group are connected so as to provide an output of the respective group;

the output of each group has an average field of view of the fields of view of the detectors of the respective group; and each detector of said plurality of groups of detectors is situated in a particular location on the structure so that the average fields of view of said plurality of groups of detectors are approximately equivalent to one another.

23. The sensor of claim 22, wherein each group has a plurality of filters proximate to the detectors of the respective group.

24. The sensor of claim 23, wherein the bandwidth of the plurality of filters for each group is different from the bandwidths of the pluralities of filters of other groups.

25. The sensor of claim 24, the detectors are infrared detectors.

26. A method for sensing comprising:

selecting a plurality of groups of detectors, wherein each group of detectors detects a particular bandwidth of radiation;

connecting the detectors of each group to provide an output from each of the respective groups;

recognizing that at least one detector has a field of view different from a field of view of another detector; and placing the detectors at locations in an array so that each group of detectors has a field of view at its output that is approximately equivalent to the fields of view at the outputs of the other groups of detectors.

27. Means for sensing comprising:

first means for detecting radiation;

at least another means for detecting radiation; and means for supporting said first means for detecting radiation and said at least another means for detecting radiation;

wherein:

said means for detecting radiation has a first field of view;

said at least another means for detecting radiation has another field of view;

said means for detecting radiation and said at least another means for detecting radiation are placed at certain locations on said means for supporting to assure that the first and other fields of view are approximately equivalent.

28. A sensor comprising:

a plurality of groups of detectors situated on a support structure; and wherein:

each detector of said plurality of groups of detectors has a field of view;

the detectors of each group of detectors are connected resulting in a field of view of the group of detectors; and the fields of view of the groups of detectors are about the same.

29. The sensor of claim 28, wherein:

the detectors of a group are sensitive to the same bandwidth;

each group of detectors is sensitive to a bandwidth that is different from a bandwidth to which another group of detectors is sensitive.

30. The sensor of claim 29, wherein:

a group of detectors has a bandwidth where substances subject to detection are transparent; and at least some of the groups of detectors have bandwidths centered on absorption lines of the substances subject to detection.

31. The sensor of claim 30, wherein:

an imbalance, between an amount of radiance detected by the group of detectors having the bandwidth where the substances subject to detection are transparent, and radiance detected by a group of detectors having a bandwidth centered on an absorption line of a substance subject to detection, indicates a presence of the substance.

32. The sensor of claim 31, further comprising a filter situated proximately on each detector wherein the filter determines the bandwidth of detection of the respective detectors.

33. The sensor of claim 32, further comprising a topcap situated on the support structure, wherein said topcap and support structure result in an integrated vacuum package enclosing said plurality of groups of detectors.

34. The sensor of claim 33, wherein each said filter situated proximately on each detector is situated in the topcap.

35. The sensor of claim 34, wherein each detector is sensitive to infrared radiation.

36. The sensor of claim 35, wherein the fields of view of the groups of detectors are directed in a pre-determined direction.

37. The sensor of claim 36, wherein the sensor is made with microelectromechanical systems (MEMS) techniques.

38. The sensor of claim 36, further comprising a sphere wherein the sphere comprises:

a first port; and a second port; and wherein:

the sphere is hollow having a reflective inner surface;

the plurality of groups of detectors situated on the support structure is situated at the second port with the fields of view directed towards the inner surface of the sphere; and the second port of the sphere has a field of view directed out from the sphere.

* * * * *